(12) United States Patent
Liu et al.

(10) Patent No.: US 11,540,868 B1
(45) Date of Patent: Jan. 3, 2023

(54) ABLATION DEVICE

(71) Applicant: HYGEA MEDICAL TECHNOLOGY CO., LTD., Beijing (CN)

(72) Inventors: Peng Liu, Beijing (CN); Weiliang Gao, Beijing (CN); Jian Xiao, Beijing (CN); Qianfu Huang, Beijing (CN)

(73) Assignee: HYGEA MEDICAL TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 17/715,018

(22) Filed: Apr. 6, 2022

(30) Foreign Application Priority Data

Jun. 30, 2021 (CN) .......................... 202110735881.1

(51) Int. Cl.
*A61B 18/02* (2006.01)
*A61B 18/00* (2006.01)

(52) U.S. Cl.
CPC .... *A61B 18/02* (2013.01); *A61B 2018/00577* (2013.01); *A61B 2018/0287* (2013.01); *A61B 2018/0293* (2013.01)

(58) Field of Classification Search
CPC ..... A61B 18/02; A61B 18/14; A61B 18/1477; A61B 2018/00577; A61B 2018/0262; A61B 2018/0287; A61B 2018/0293; A61B 2018/1425
USPC ...................................... 606/21–26
See application file for complete search history.

(56) References Cited

U.S. PATENT DOCUMENTS

| 4,802,475 A | 2/1989 | Weshahy | |
| 2005/0038422 A1* | 2/2005 | Maurice | A61B 18/02 606/23 |
| 2008/0114345 A1 | 5/2008 | Arless et al. | |
| 2012/0089047 A1* | 4/2012 | Ryba | A61B 18/02 600/300 |

FOREIGN PATENT DOCUMENTS

| CN | 209032618 U | 6/2019 |
| CN | 110575242 A | 12/2019 |
| CN | 210019627 U | 2/2020 |
| CN | 210019629 U | 2/2020 |
| CN | 212281606 U | 1/2021 |
| CN | 213190035 U | 5/2021 |
| CN | 112932657 A | 6/2021 |

* cited by examiner

*Primary Examiner* — Khadijeh A Vahdat

(57) ABSTRACT

The present disclosure relates to an ablation device, which relates to the technical field of cryoablation treatments, and is used for solving the technical problem of an excessive burden on an operator caused by the volume of a delivery device being too large. The ablation device of the disclosure comprises an ablation needle and a working medium transmission device connected to the ablation needle. The working medium transmission device comprises a first delivery tube and a second delivery tube. The first delivery tube and the second delivery tube are configured to be of split structures that are independent of each other, such that the structure of the working medium delivery device at the rear end of the ablation needle is smaller and lighter, and thus the burden on the operator's operation can be reduced, making the operation to be more flexible and convenient.

9 Claims, 20 Drawing Sheets

182

ABLATION DEVICE

CROSS REFERENCE TO RELATED APPLICATIONS

The present application claims the priority of Chinese patent application 202110735881.1, filed on Jun. 30, 2021 and entitled "Ablation device", which is incorporated herein by reference in its entirety.

FIELD OF THE INVENTION

The present disclosure relates to the technical field of cryoablation treatment, and in particular to an ablation device.

BACKGROUND OF THE INVENTION

Ablation is the surgical medical technology where a target tissue is eliminated by using a freezing and a thermal medium. During a surgical operation, it is necessary to convey a freezing medium to a lesion region of a patient in order to take away the heat of a lesion tissue via evaporation and heat absorption of the freezing medium, so that the temperature of a target ablation position is decreased, thereby destroying pathological cells and tissues and achieving a treatment purpose. After the cryotherapy is completed, a thermal medium is controlled for delivery to the lesion region of a patient, which instantaneously releases a large amount of heat, such that the temperature of a treatment region is rapidly recovered. The treatment media (a freezing and a thermal medium) are conveyed by a delivery device, which has an input line and a backflow line. An input line and a backflow line of an existing delivery device are integrated into the same tube, which causes the delivery device to be relatively heavy, increasing an additional burden on a user's operation.

SUMMARY OF THE INVENTION

The disclosure provides an ablation device for solving the technical problem of an excessive burden on an operator caused by the volume of a delivery device being too large.

The disclosure provides an ablation device, including an ablation needle and a working medium transmission device connected to the ablation needle, wherein the working medium transmission device includes a first delivery tube, which is used for delivering a working medium to an ablation needle;

a second delivery tube, which is used for receiving and discharging a working medium that is output from the ablation needle after treatment is performed; and a connection tube, a first end of which is connected to the ablation needle, and a second end of which is respectively connected to the first delivery tube and the second delivery tube;

wherein the first delivery tube and the second delivery tube are configured to be of split structures that are independent of each other.

In one embodiment, the second delivery tube includes an outer cannula, which is arranged at a side of the connection tube that is away from the ablation needle, where a heat exchange device is arranged in the outer cannula; and a second conduit, at least part of the second conduit extending from the second end of the connection tube into the connection tube, and at least part of the second conduit extending into the outer cannula and is connected to the heat exchange device, so that the working medium in the ablation needle after the treatment is performed can be delivered to the heat exchange device through the second conduit, and the working medium after being subjected to heat exchange in the heat exchange device can directly be discharged into the environment.

In one embodiment, the heat exchange device is internally provided with a path for the flowing of the working medium after the treatment is performed. One end of the path is in communication with the second conduit, and the other end thereof is in communication with the environment.

The path includes one or more of a spiral path, a snakelike path, a clip-shaped path, and a waved path.

In one embodiment, the second end of the connection tube is also provided with a diffluence device, the diffluence device including a seal, which is arranged at the second end of the connection tube in a sealing manner;

a first through hole, which is provided in the seal and axially passes through the seal for being connected to the first delivery tube in a fitting manner;

a protrusion portion, which axially extends from an end portion of the seal for being engaged with an inner wall of the outer cannula; and a second through hole, which is provided in the seal and axially passes through the seal and the protrusion portion for being connected to the second conduit in the fitting manner.

In one embodiment, the connection tube is internally provided with a conflux device that is in communication with the ablation needle. The first delivery tube and the second delivery tube respectively extend from the second end of the connection tube into the connection tube and are in communication with the conflux device, so as to deliver a working medium into the ablation needle or receiving the working medium from the ablation needle.

In one embodiment, the conflux device includes a conflux tube arranged in the connection tube. A first end of the conflux tube extends out of the connection tube and is connected to a quick coupling, and the quick coupling is connected to the ablation needle in the fitting manner.

A second end of the conflux tube is provided with a first connection hole for being connected to the first delivery tube in the fitting manner, and a second connection hole for being connected to the second conduit in the fitting manner. The first connection hole and the second connection hole are arranged side by side in the radial direction of the conflux tube.

The conflux tube is also internally provided with a drainage hole, with the drainage hole being connected to the first connection hole in a lapped manner.

In one embodiment, the quick coupling includes a fitting hole that is connected to the ablation needle in the fitting manner. At least part of an inner wall of the fitting hole in the axial direction tapers, so as to form tapered sealing with a sealing ring on the ablation needle.

In one embodiment, the ablation needle includes a needle body and a handle, which are in connection via a sealing connection interface. The sealing connection interface is provided in the handle, the sealing connection interface includes a first opening and a second opening, which are arranged in one metal tube, and a line in the needle body sequentially passes through the first opening and the second opening.

The sealing connection interface also includes a vacuum sealed opening provided in the circumferential direction of the first opening. The vacuum sealed opening includes a large hole and a small hole, which are configured to be stepped holes. The axes of the large hole and the small hole are in parallel to the axis of the first opening, and the small hole is in communication with the second opening.

In one embodiment, the needle body includes
an inflow tube, which is in communication with the first delivery tube, and includes a treatment tube section and a non-treatment tube section;
a cannula, which is sheathed at the treatment tube section of the inflow tube; and
a vacuum cannula, which is sheathed at the non-treatment tube section of the inflow tube.

The cannula is configured to be a plastic hose or a flexible metal hose.

The treatment tube section is provided with a plurality of formation holes. A working medium in the treatment tube section flows to a space between the treatment tube section and the cannula through the formation holes, so that icicles for treatment can be formed on an outer wall of the cannula.

In one embodiment, the plurality of formation holes are distributed in the following one or more manners.

The plurality of formation holes are provided at equal intervals in the axial direction of the treatment tube section, and one or more formation holes are provided on one and the same radial cross-section of the treatment tube section.

The plurality of formation holes are provided in a clockwise or counterclockwise spiral manner in the circumferential direction of the treatment tube section.

In one embodiment, the aperture d2 of each formation hole is 0.3 mm to 0.4 mm, and/or
the spacing between the adjacent formation holes in the axial direction is 6 mm to 12 mm Compared with an existing technique, the advantages of the disclosure are as follows. Differing from the technical solution in the existing technique of integrating two delivery tubes in one tube, in the disclosure, a first delivery tube for delivering a working medium to an ablation needle and a second delivery tube for receiving the working medium from the ablation needle are provided to be of split structures which are independent of each other. Due to such special split structures, the structure of a working medium transmission device at a rear end of the ablation needle is lighter, such that the burden on an operator's operation can be reduced, and the operation is more flexible and convenient.

BRIEF DESCRIPTION OF THE DRAWINGS

The disclosure will be described in more details below based on embodiments and referring to the accompanying drawings.

LIST OF REFERENCE SIGNS

Figure 1:
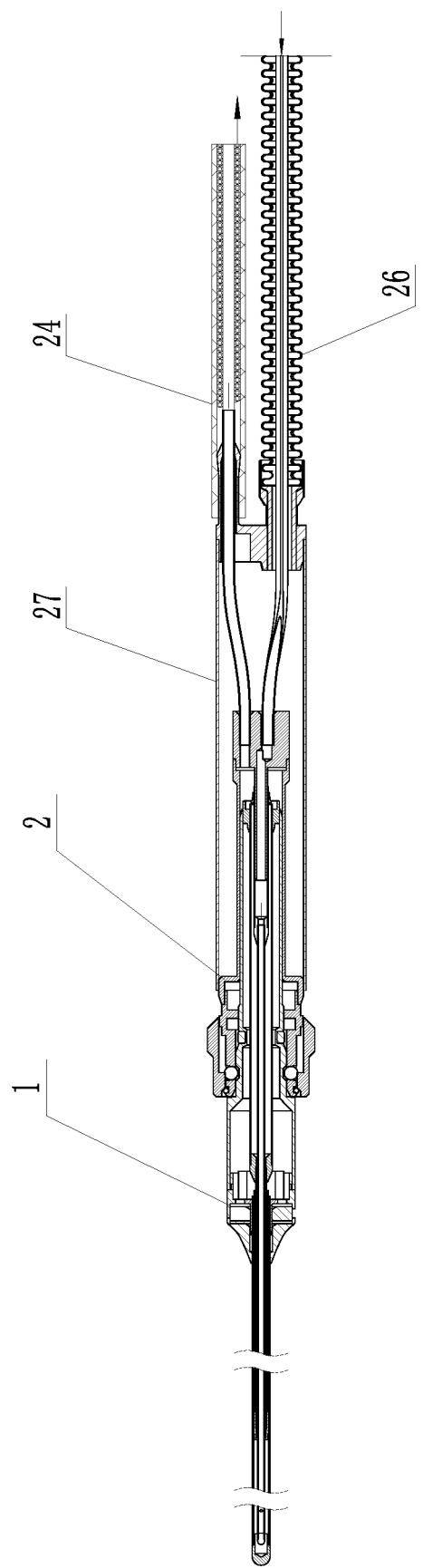
FIG. 1 is a cutaway view of an ablation device in an embodiment of the disclosure.

1-Ablation needle;
11-Quick male coupling; 12-Handle; 13-Temperature transmitter; 14-Temperature display device;
15-Sealing connection interface; 151-First opening; 152-Second opening; 153-Vacuum sealing opening; 153a-Large hole; 153b-Small hole;
16-Sealing ring; 17-Protective sleeve; 18-Needle body;
181-Inflow tube; 181a-Treatment tube section; 181b-Formation hole;
182-Cannula; 183-Vacuum cannula; 184-Temperature measurement thermocouple;
2-Working medium transmission device;
21-Quick coupling; 211-Fitting hole;
22-Conflux device; 221-Conflux tube; 221a-First connection hole; 221b-Second connection hole; 221c-Drainage hole;
23-Diffluence device; 231-Seal; 232-First through hole; 233-Protrusion portion; 234-Second through hole;
24-Second delivery tube; 241-Outer cannula; 242-Second conduit; 243-Fixing tube;
25-Heat exchange device; 251-Path; 252-Spiral fin; 253-Column body; 254-Partition plate;
26-First delivery tube; 261-Flexible cannula; 262-First conduit; 263-Transition joint;
27-Connection tube.

DETAILED DESCRIPTION OF THE EMBODIMENTS

The disclosure will be further described below in conjunction with the accompanying drawings.

As shown in FIGS. 1-20, the disclosure provides an ablation device, including an ablation needle 1 and a working medium transmission device 2 connected to the ablation needle 1. The working medium transmission device 2 delivers a working medium for treatment to the ablation needle 1. The ablation needle 1 performs cryoablation treatment in a target area by using the working medium. The working medium after the treatment is performed returns to the working medium transmission device 2 from the ablation needle 1. The working medium transmission device 2 can choose to directly discharge or recover the working medium after the treatment is performed.

It should be noted that the working medium for treatment as described in the disclosure is a cold working medium (e.g. liquid nitrogen) and a heat working medium (e.g. absolute ethyl alcohol). It should be understood that known working mediums used in other ablation treatment can also be used, which will not be described in the disclosure.

The working medium transmission device 2 of the disclosure will be described below in details in conjunction with FIGS. 1-10.

The working medium transmission device 2 includes a first delivery tube 26, a second delivery tube 24 and a connection tube 27. The first delivery tube 26 is used for delivering a working medium to the ablation needle 1. The second delivery tube 24 is used for receiving and discharging a working medium that is output from the ablation needle 1 after treatment is performed. A first end of the connection tube 27 is connected to the ablation needle 1, and a second end of the connection tube 27 is respectively connected to the first delivery tube 26 and the second delivery tube 24.

Figure 2:
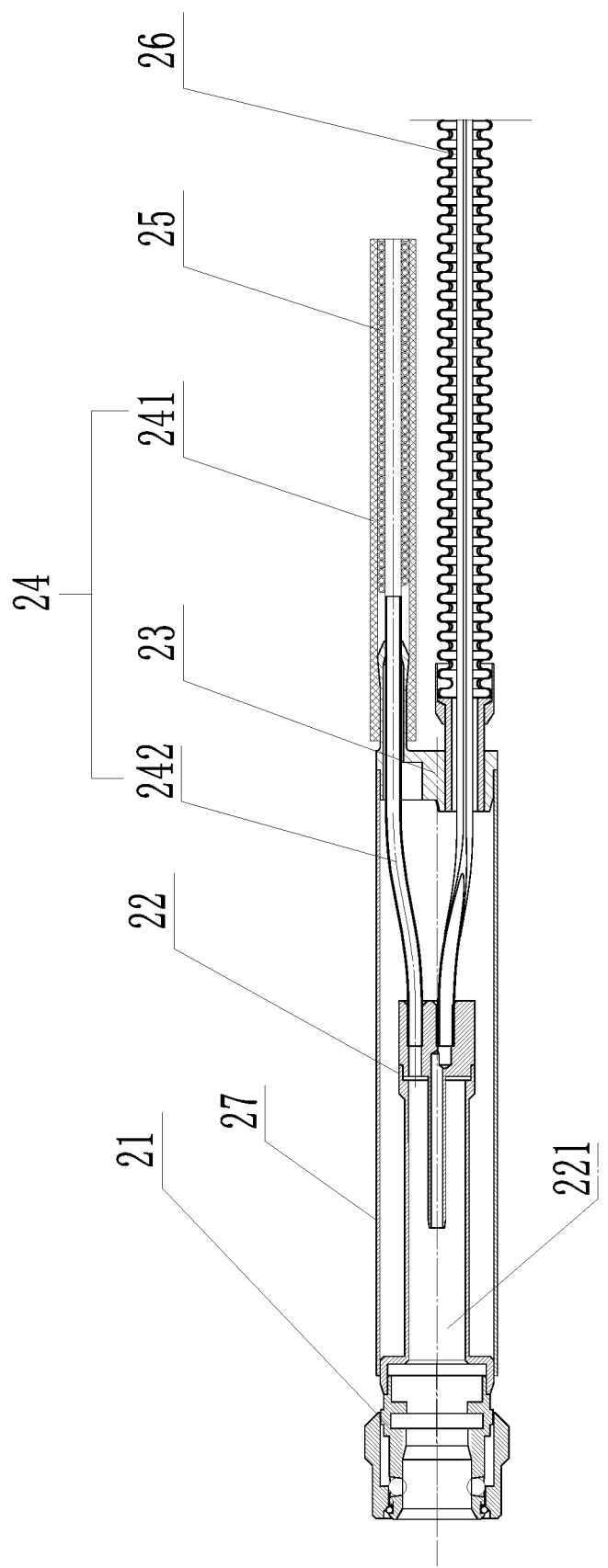
FIG. 2 is a cutaway view of a working medium transmission device as shown in FIG. 1.

As shown in FIGS. 1 and 2, the first delivery tube 26 and the second delivery tube 24 are configured to be of split structures which are independent of each other. In other words, passages for delivering a working medium to the ablation needle 1 and receiving a working medium from the ablation needle 1 in the disclosure are paths which are independent of each other. All the delivery devices in an existing technique deliver a working medium in such a way that an inner metal tube and an outer metal tube are arranged in one metal tube to form an inflow path and a backflow path. When a delivery line is relatively long, the device is relatively heavy, and the operation is relatively difficult. Therefore, compared with the structure of an inflow passage and a backflow passage being arranged in one metal tube in the existing technique, the independent split structure of the disclosure can enable the structure of the connection tube 27 connected to the ablation needle 1 to be light, so as to reduce the burden on a doctor's operation, such that the operation is simpler and more flexible, which can simplify the production process, improve the production efficiency, and reduce the production cost.

Figure 3:
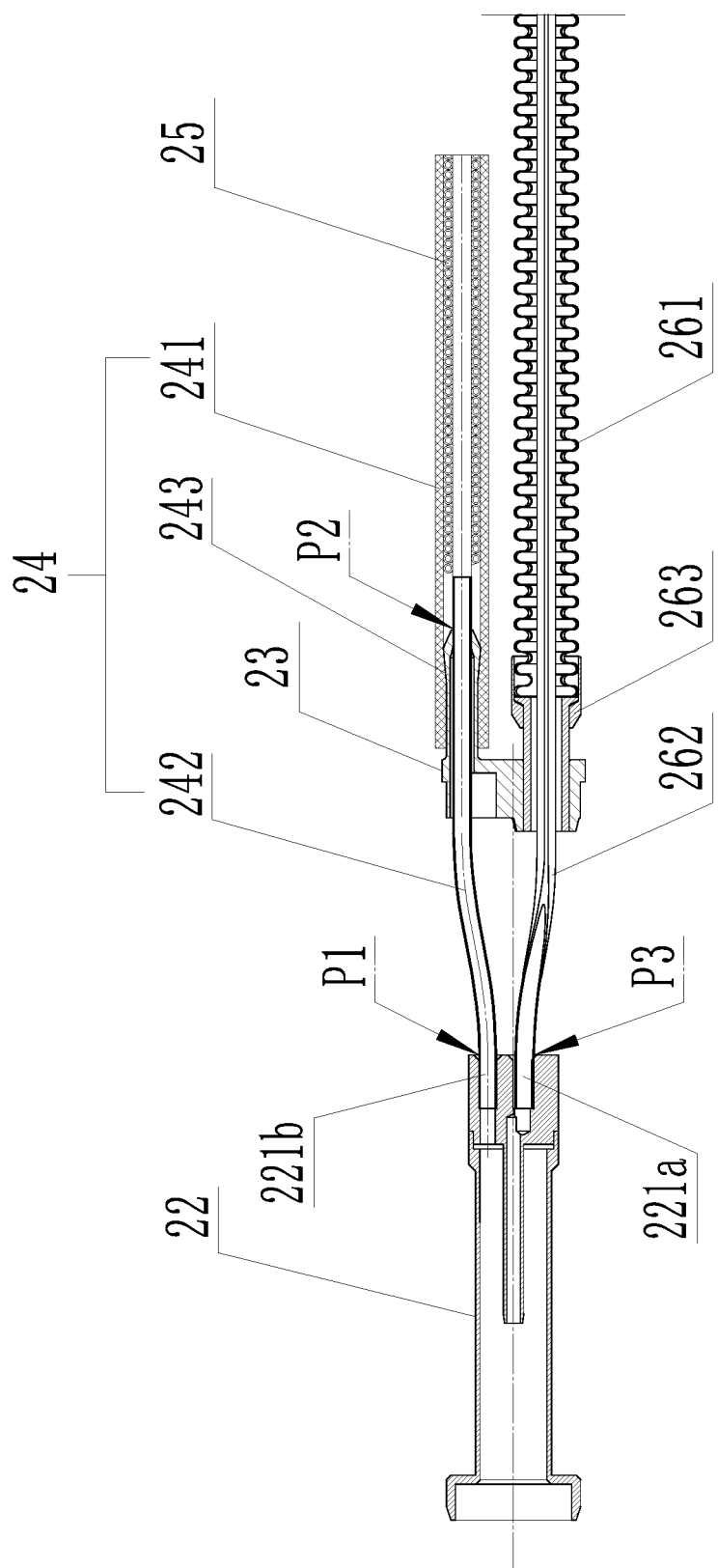
FIG. 3 is a cutaway view of a second delivery tube as shown in FIG. 2.
Figure 4:
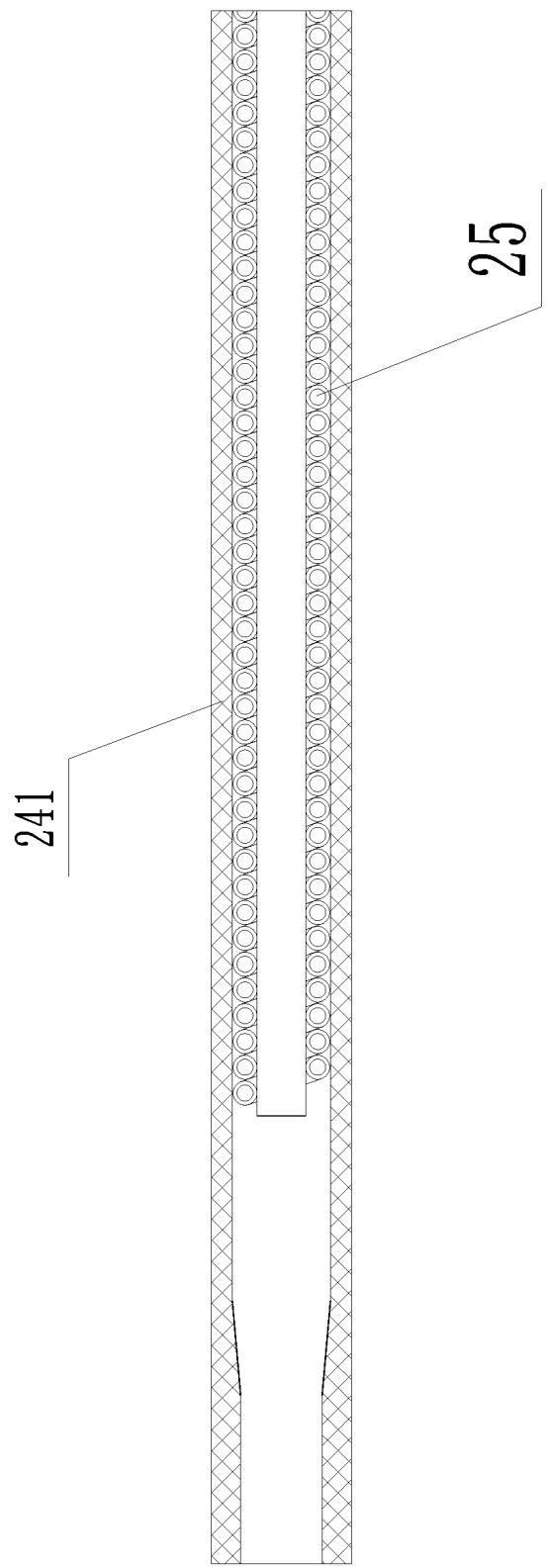
FIG. 4 is a cutaway view of a heat exchange device as shown in FIG. 2.

In particular, the second delivery tube 24 includes an outer cannula 241 and a second conduit 242. As shown in FIGS. 2 and 3, the outer cannula 241 is arranged at a side of the connection tube 27 that is away from the ablation needle 1, and a heat exchange device 25 is arranged in the outer cannula 241 (as shown in FIG. 4). The second conduit 242 is fixedly connected to the outer cannula 241 via the fixing tube 243. As shown in FIG. 3, the second conduit 242 is connected to the fixing tube 243 in a welded manner at a position P2.

As shown in FIG. 2, at least part (e.g. a first end) of the second conduit 242 extends from the second end of the connection tube 27 into the connection tube 27, and at least part (e.g. a second end) of the second conduit 242 extends into the outer cannula 241 and is connected to the heat exchange device 25, so that the working medium in the ablation needle 1 after the treatment is performed can be delivered to the heat exchange device 25 through the second conduit 242, and the working medium after being subjected to heat exchange in the heat exchange device 25 can directly be discharged into the environment. Since the working medium has been subjected to heat exchange in the target area, the temperature of the working medium after treatment is performed increases. In order to achieve the aim of facilitating the operation, the working medium after being subjected to heat exchange is enabled to pass through the heat exchange device 25, so that the temperature of the working medium tends to be the room temperature, and thus the working medium can be directly discharged into the environment. Therefore, the outer cannula 241 does not need to be set too long and does not need to be connected to the working medium transmission device 2.

With regard to the cold working medium (e.g. liquid nitrogen or a mixture of liquid nitrogen and nitrogen) after the treatment is performed, the temperature is relatively low. If the low-temperature working medium is directly discharged, the working medium may frostbite relevant personnel to cause unnecessary personal injury, and the phenomenon of "white smoke" may occur when the low-temperature working medium is discharged, which phenomenon will exert great mental stress on the doctor and the patient, thereby affecting a surgery. Therefore, it is necessary to process the cold working medium after the treatment is performed so that the cold working medium tends to be the room temperature in order to directly discharge the cold working medium.

Similarly, with regard to the heat working medium (e.g. absolute ethyl alcohol) after the treatment is performed, the temperature is relatively high. If the heat working medium is directly discharged, the heat working medium may burn relevant personnel to cause unnecessary personal injury. Therefore, it is necessary to further process the heat working medium in order to directly discharge the heat working medium.

Therefore, the heat exchange device 25 is provided, so as to increase the temperature of the liquid nitrogen working medium after the treatment is performed, and the liquid nitrogen converts into nitrogen, which can be directly discharged into the environment, without the need to provide a recovery device. Therefore, the miniaturization and light-weighting of the working medium transmission device 2 can be further improved.

Furthermore, since the liquid nitrogen working medium passes through the heat exchange device 25, after the working medium is subjected to heat exchange with the heat exchange device 25, the temperature of the working medium increases, whereas the temperature of the heat exchange device 25 decreases. At this time, the heat working medium after the treatment is performed is enabled to pass through the heat exchange device 25 for heat exchange, so that the temperature of the heat working medium after being subjected to heat exchange with the heat exchange device 25 can decrease to tend to be the room temperature. In reverse, since the temperature of the heat exchange device 25 increases when the heat working medium passes through the heat exchange device 25, the heat exchange of the heat exchange device 25 with a liquid nitrogen working medium next time is facilitated.

In order to achieve the aim of the temperature of the working medium after the treatment is performed tending to be the room temperature so that the working medium can be directly discharged, the heat exchange device 25 is internally provided with a path 251 for the flowing of the working medium after the treatment is performed. One end of the path 251 is in communication with the second conduit 242, and the other end of the path 251 is in communication with the environment. The path 251 includes one or more of a spiral path, a snakelike path, a clip-shaped path, and a waved path.

Figure 5:
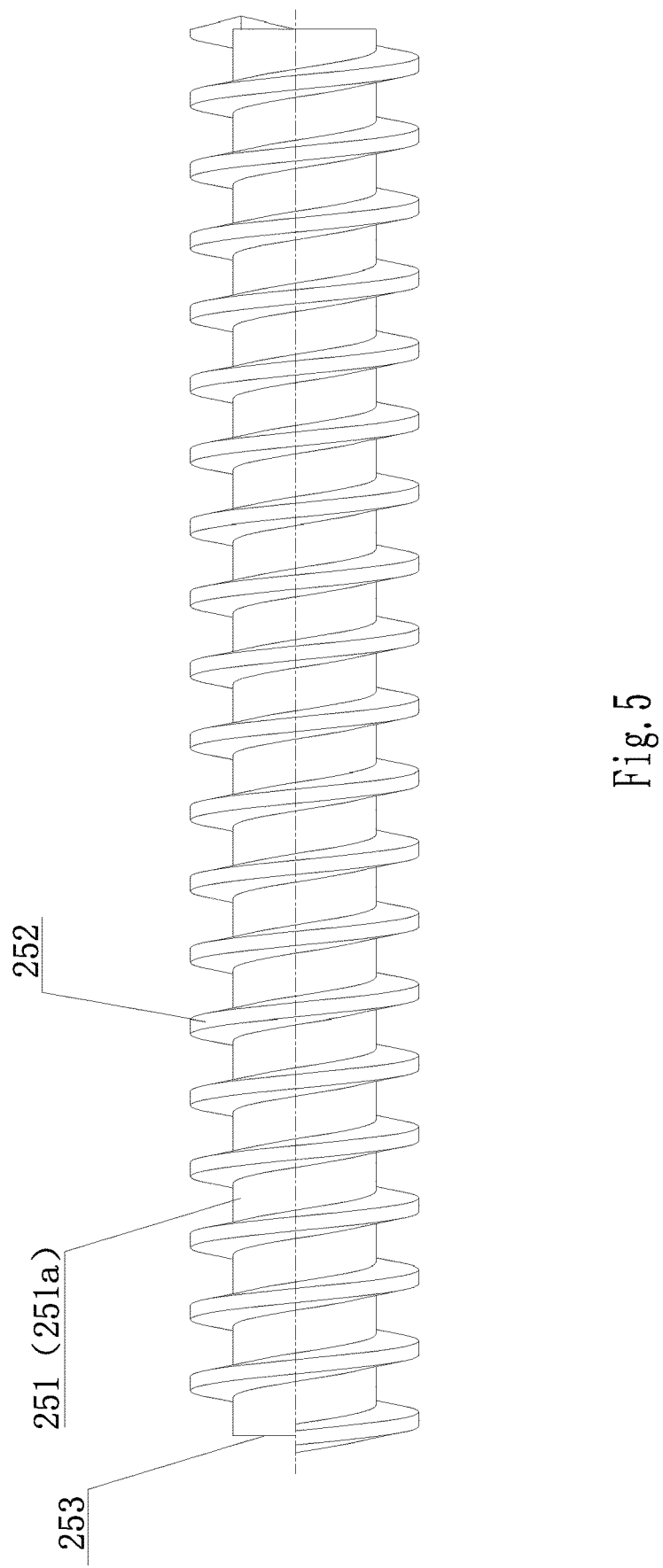
FIG. 5 is a schematic diagram of a three-dimensional structure of a spiral path in one of the embodiments of the disclosure.

In the embodiment as shown in FIG. 5, the path 251 is configured to be a spiral path 251a. In particular, the heat exchange device 25 includes a column body 253 arranged in the outer cannula 241, and a spiral fin 252 spirally extending on an outer wall of the column body 253 in the axial direction thereof. The axis of the column body 253 coincides with the axis of the outer cannula 241. An edge of the spiral fin 252 is in contact with an inner wall of the outer cannula 241. Thus, the part between the outer wall of the column body 253 and the inner wall of the outer cannula 241 is configured to be the spiral path 251*a*.

The second conduit 242 is in communication with the spiral path 251*a*, and thus the working medium after the treatment is performed can enter the spiral path 251*a* through the second conduit 242. The spiral path 251*a* is provided, so as to elongate a flowing path of the working medium after the treatment is performed in the heat exchange device 25, such that the duration for which the working medium stays in the heat exchange device 25 becomes longer. Therefore, the temperature of the working medium, after the treatment is performed, after flowing through the spiral path 251*a* can tend to be the room temperature, and thus the requirement of direct discharge can be met.

Furthermore, the outer cannula 241 can be configured to be a plastic hose, and the spiral fin 252 can form interference fit with the inner wall of the outer cannula 241. In other words, there is no gap between the spiral fin 252 and the inner wall of the outer cannula 241, thereby ensuring that the working medium after the treatment is performed completely enters the spiral path 251*a*.

Figure 6:
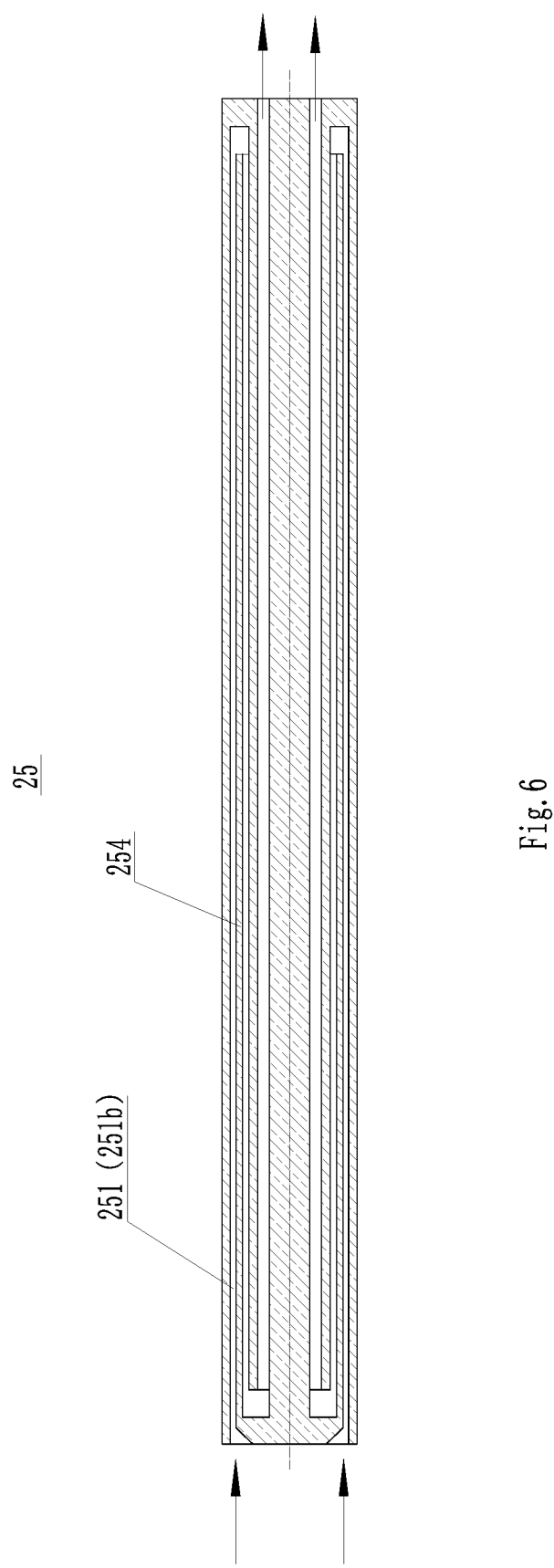
FIG. 6 is a cutaway view of a snakelike path in another embodiment of the disclosure.

Preferably, the spiral fin 252 is made of a material having a great heat exchange coefficient (e.g. copper, aluminum, etc.). In the embodiment as shown in FIG. 6, the path 251 is configured to be the snakelike path (also referred to as a Z-shaped path and a zigzag path) 251*b*. In particular, the heat exchange device 25 includes a plurality of partition plates 254 extending along the axis of the outer cannula 241, and the snakelike path 251*b* for the flowing of a medium is formed between the partition plates 254.

As shown in FIG. 6, the working medium enters through the first end of the heat exchange device 25, flowing to the second end to reach a tail end of the second end and turning back, and after turning back, flows to the first end to reach a tail end of the first end and then turns back again. By such reciprocation, the aim of lengthening the flowing path of the working medium after the treatment is performed in the heat exchange device 25 is achieved, such that the duration for which the working medium stays in the heat exchange device 25 becomes longer. Therefore, the temperature of the working medium, after the treatment is performed, after flowing through the snakelike path 251*b* can tend to be the room temperature, and thus the requirement of direct discharge can be met. In this way, the structure of the rear end of the ablation needle 1 can be better optimized, and the weight of the structure of the rear end is obviously reduced, thereby improving the usability.

In some optional embodiments, the path 251 can be a waved path. The waved path can be one of or a combination of a sinusoidal waved path, a cosinoidal waved path and a square waved path. The waved path can be configured by partition plates having protrusions and recesses that are staggered.

In some optional embodiments, the path 251 can be a combination of any of a spiral path, a snakelike path, a clip-shaped path, and a waved path. For example, the path 251 can be a combination of a spiral path and a snakelike path, where the spiral path and the snakelike path are mutually connected in series, thereby further enlarging the flowing path of the working medium to reduce the temperature of the working medium.

In the various embodiments above, the length of the path 251, the flowing manner, etc. can all be adjusted according to an output time in order to satisfy a heat exchange requirement (a requirement for the temperature during discharging).

Furthermore, the heat exchange device 25 can also be connected to a heating device. For example, in the preferred embodiment above, the spiral fin 252 or the column body 253 is connected to the heating device, so as to increase the temperature of the heat exchange device 25, so that liquid nitrogen and the heat exchange device 25 can efficiently perform heat exchange. For another example, in the optional embodiment above, the partition plates 254 are connected to the heating device, so as to increase the temperature of the heat exchange device 25. The heating device can use an existing heating method, such as a resistance wire.

It should be noted that the path 251 of the disclosure is not limited to the embodiments above, any solution of decreasing the temperature of the working medium by lengthening the flowing path of the working medium should be deemed to fall within the scope of protection of the disclosure. The input path and the output path in the ablation needle 1 are arranged in one metal tube to be of an integrated structure, and therefore, in order to realize the split configuration of the first delivery tube 26 and the second delivery tube 24, the first delivery tube 26 and the second delivery tube 24 requires conflux in the connection tube 27, and diffluence at the second end of the connection tube 27.

In particular, the conflux of the first delivery tube 26 and the second delivery tube 24 is performed via the conflux device 22, and the diffluence is performed via the diffluence device 23.

The conflux device 22 is arranged inside the connection tube 27 and is in communication with the ablation needle 1. The first delivery tube 26 and the second delivery tube 24 respectively extend from the second end of the connection tube 27 into the connection tube 27 and are in communication with the conflux device 22, so as to deliver a working medium into the ablation needle 1 or receiving the working medium from the ablation needle 1.

Figure 7:
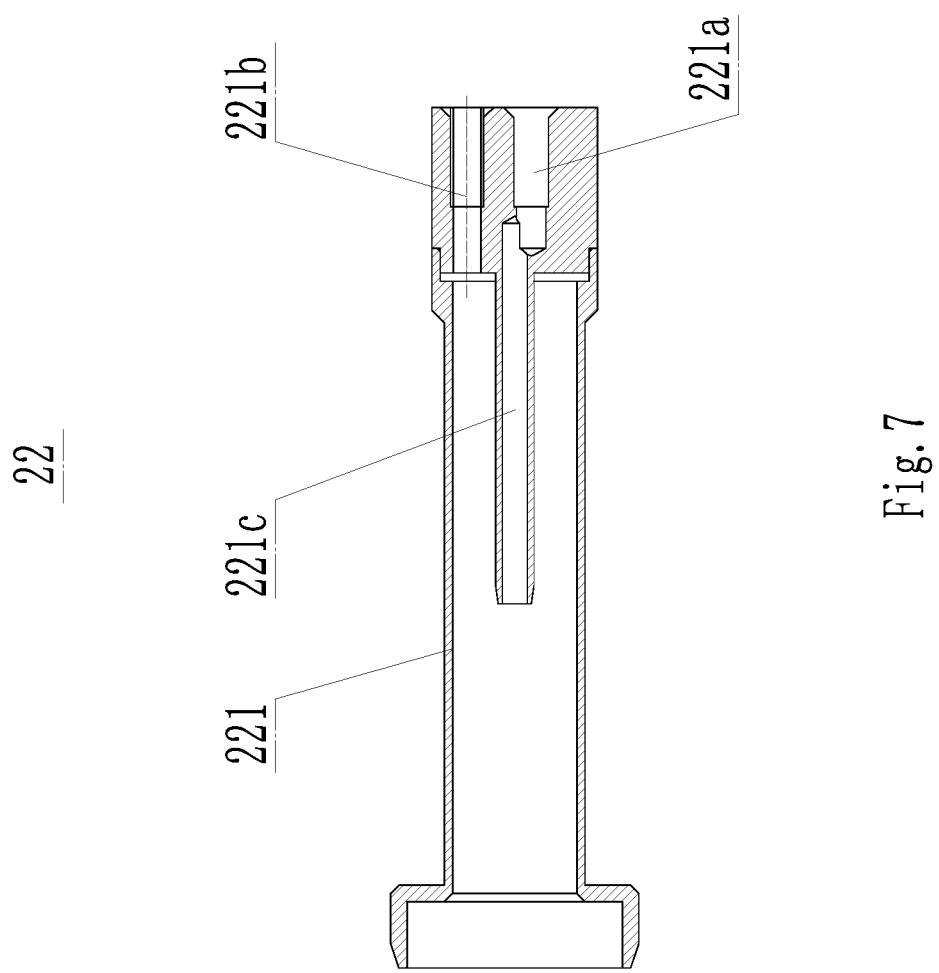
FIG. 7 is a cutaway view of a conflux device as shown in FIG. 2.

As shown in FIG. 2 and FIG. 7, the conflux device 22 includes a conflux tube 221 arranged in the connection tube 27. A first end of the conflux tube 221 extends out of the connection tube 27 and is connected to a quick coupling 21, and the quick coupling is used for being connected to the ablation needle 1 in the fitting manner.

A second end of the conflux tube 221 is provided with a first connection hole 221*a* for being connected to the first delivery tube 26 in the fitting manner, and a second connection hole 221*b* for being connected to the second conduit 242 in the fitting manner. The first connection hole 221*a* and the second connection hole 221*b* are arranged side by side in the radial direction of the conflux tube 221. As shown in FIG. 7, the axis of the first connection hole 221*a* and the axis of the second connection hole 221*b* are respectively located at two sides of the axis of the conflux tube 221.

Furthermore, the conflux tube 221 is also internally provided with a drainage hole 221*c*, with the drainage hole 221*c* being connected to the first connection hole 221*a* in a lapped manner. As shown in FIG. 7, the axis of the drainage hole 221*c* coincides with the axis of the conflux tube 221. Referring to FIG. 1, the axial direction of the ablation needle 1 coincides with the axial direction of the working medium transmission device 2, and therefore, the axis of the drainage hole 221c coincides with axis of the ablation needle 1, such that the drainage hole 221c can be connected to a corresponding component of the ablation needle 1 in the fitting manner. In addition, the drainage hole 221c is provided at a central axis position, and after the drainage hole 221c is connected to the corresponding component of the ablation needle 1 in the fitting manner, the ablation needle 1 can rotate around the axis of the drainage hole 221c.

Differing from the alignment connection between two holes, in the disclosure, the drainage hole 221c and the first connection hole 221a only partially overlap with each other in the axial direction. As shown in FIG. 7, the axial direction of the first connection hole 221a and the axial direction of the drainage hole 221c are staggered with each other, and thus the space can be saved, such that the first connection hole 221a and the second connection hole 221b can provided in a narrow space while the two do not interfere with each other.

After conflux is performed at the conflux device 22, it is necessary to perform diffluence at an end portion of the connection tube 27, so as to realize the first delivery tube 26 and the second delivery tube 24 that are separately configured. Referring to FIG. 2 and FIG. 3, in order to achieve the aim of diffluence, the diffluence device 23 is arranged at the second end of the connection tube 27. In particular, as shown in FIG. 8, the diffluence device 23 includes a seal 231, a first through hole 232, a protrusion portion 233 and a second through hole 234.

The seal 231 is arranged at the second end of the connection tube 27 in a sealing manner. The first through hole 232 is provided in the seal 231 and axially passes through the seal 231 for being connected to the first delivery tube 26 in a fitting manner. The protrusion portion 233 axially extends from an end portion of the seal 231 for being engaged with an inner wall of the outer cannula 241. The second through hole 234 is provided in the seal 231 and axially passes through the seal 231 and the protrusion portion 233 for being connected to the second conduit 242 in the fitting manner.

Figure 8:
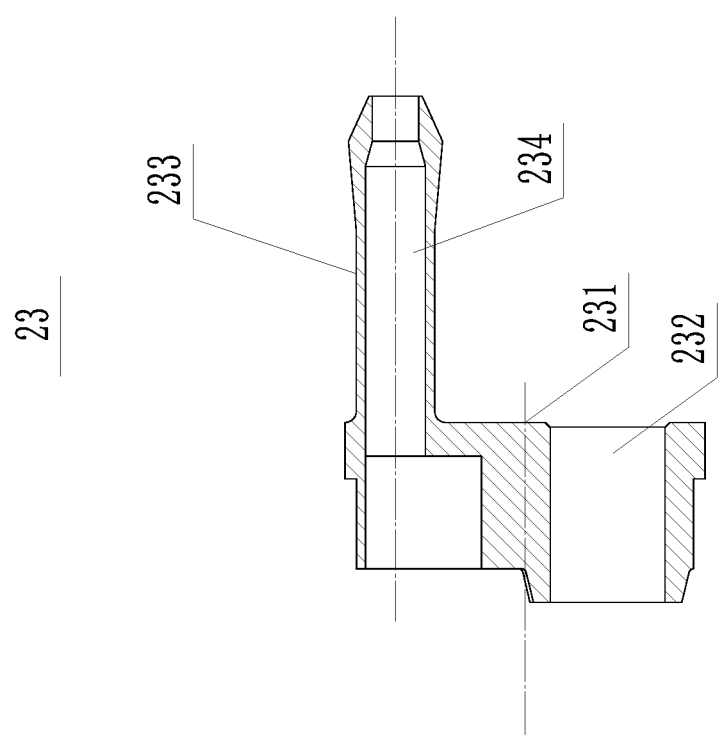
FIG. 8 is a cutaway view of a diffluence device as shown in FIG. 2.

As shown in FIG. 8, the axis of the first through hole 232 and the axis of the second through hole 234 are respectively located on upper and lower sides of the axis of the seal 231, which is also the axis of the connection tube 27, and thus the first delivery tube 26 and the second delivery tube 24 are two separate units at the second end of the connection tube 27, such that the volume and the weight of the entire device can be reduced, thereby better facilitating the operator in operations.

Figure 9:
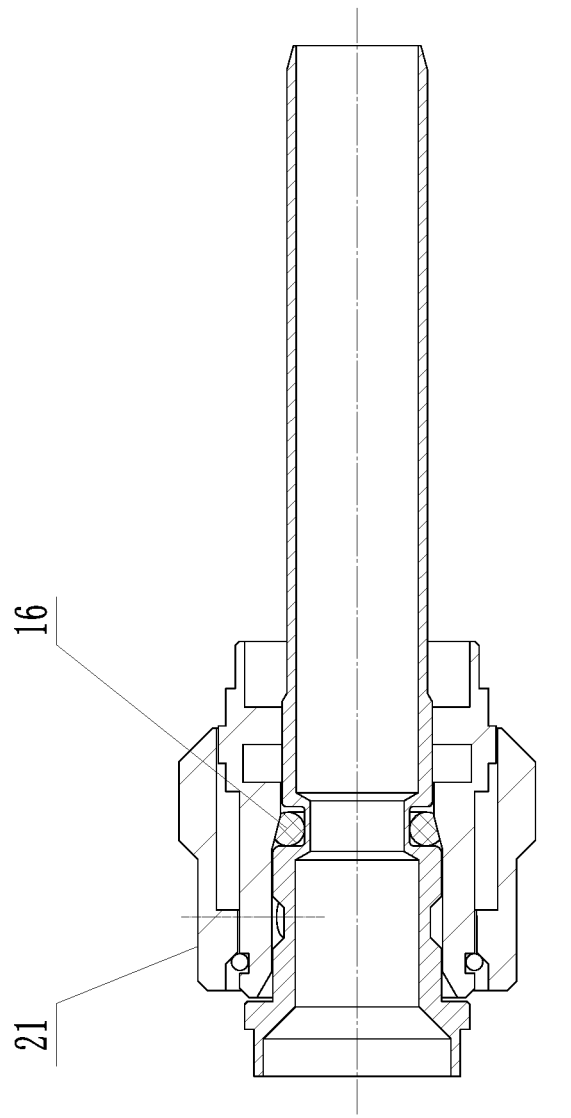
FIG. 9 is a schematic diagram of the fitting of a quick coupling as shown in FIG. 2.
Figure 10:
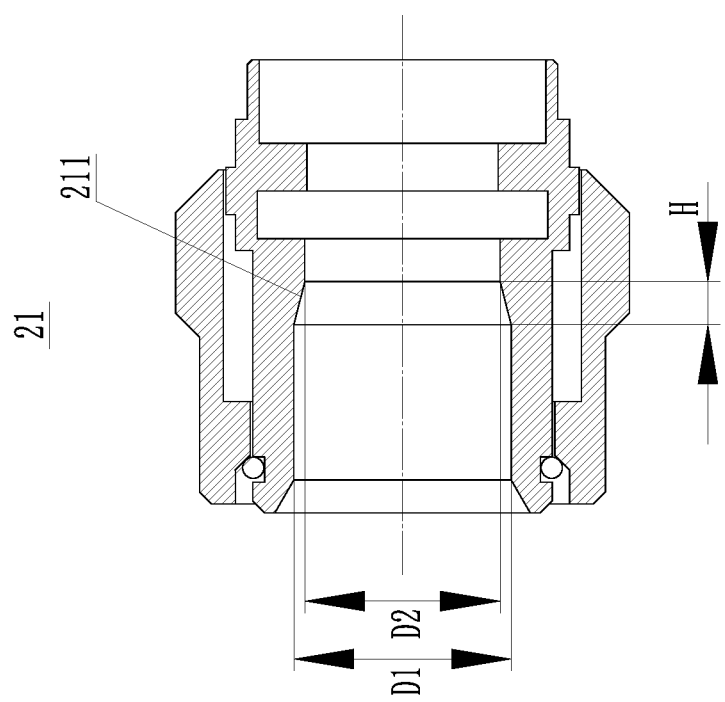
FIG. 10 is a cutaway view of the quick coupling as shown in FIG. 2.

As shown in FIG. 2, the first end of the conflux tube 221 extends out of the connection tube 27 and is connected to the quick coupling 21, and the quick coupling 21 is used for being connected to the ablation needle 1 in the fitting manner. As shown in FIG. 8 to FIG. 10, the quick coupling 21 includes a fitting hole 211 that is connected to the ablation needle 1 in the fitting manner. At least part of an inner wall of the fitting hole 211 in the axial direction tapers, so as to form tapered sealing with the sealing ring 16 on the ablation needle 1. Preferably, the tapering value (D1-D2): H herein is 1:2. That is, the the ratio of the difference value between D1 and D2 to H is 1:2. Herein, D1 is the maximum diameter of the fitting hole 211, D2 is the minimum diameter of the fitting hole 211, and H is the axial distance between the maximum diameter position and the minimum diameter position of the fitting hole 211.

Furthermore, the diameter of at least part of the inner wall of the fitting hole 211 tapers in the direction away from the ablation needle 1. Therefore, when a component on the ablation needle 1 is fitted with the ablation needle 1, a pushing-in force applied to the ablation needle 1 is reduced due to a guide function of the taper. Therefore, the operation of the operator can be facilitated, and the displacement of the needle body 18 caused by an excessive pushing-in force can also be avoided. In addition, the tapering part is used for being fitted with the sealing ring 16 located on the ablation needle 1 as described below (see FIG. 9), and therefore, the closer the ablation needle 1 gets to the quick coupling 21, the tighter the fitting between the ablation needle 1 and the quick coupling 21, such that the tight fitting between the ablation needle 1 and the quick coupling 21 can be realized without the user applying a large force. Similarly, when the ablation needle 1 is separated from the working medium transmission device 2, the tapering inner wall of the fitting hole 211 can also reduce the connection resistance, so as to reduce a traction force applied by the ablation needle 1 when moving off, such that the ablation needle 1 can be easily separated from the working medium transmission device 2 while the displacement of the needle body 18 is avoided.

Referring to FIG. 3, the first delivery tube 26 includes a flexible cannula 261 located outside the second end of the connection tube 27, a first conduit 262 arranged in the flexible cannula 261 and extending into the connection tube 27, and a transition joint 263 fixing the flexible cannula 261 to the diffluence device 23. The first conduit 262 is connected to the first connection hole 221a in the welding manner at the position P3 as shown in FIG. 3, and the second conduit 242 is connected to the second connection hole 221b in the welding manner at a position P1 as shown in FIG. 3, so as to ensure the stability of the connections.

The flexible cannula 261 can be a non-metal hose, and vacuumizing processing is performed between the flexible cannula 261 and the first conduit 262, so as to perform thermal insulation on the working medium in the first conduit 262.

The ablation needle 1 of the disclosure will be described below in details in conjunction with FIGS. 11-20.

Figure 11:
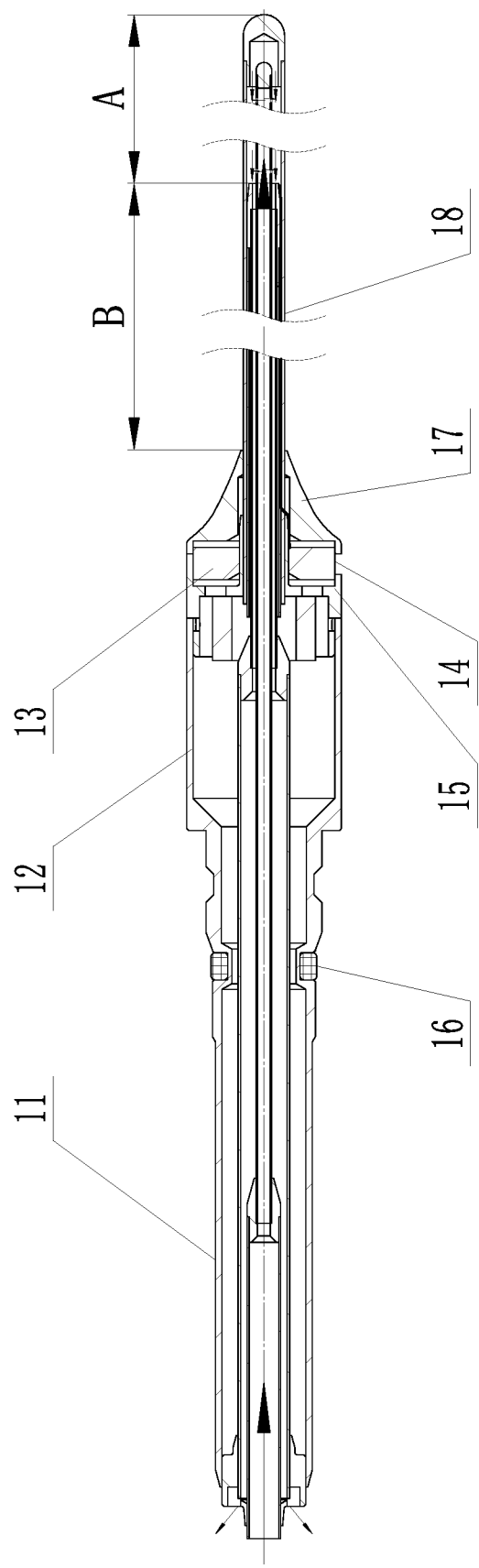
FIG. 11 is a cutaway view of an ablation needle as shown in FIG. 1.
Figure 12:
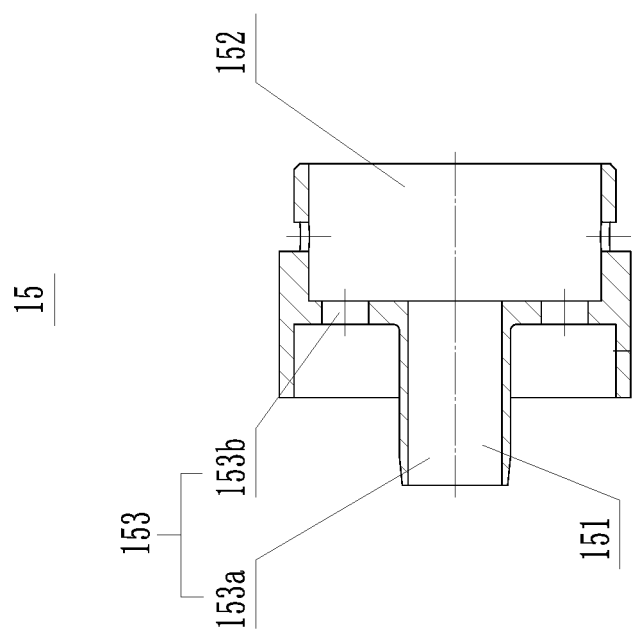
FIG. 12 is a cutaway view of a sealing connection interface as shown in FIG. 11.
Figure 13:
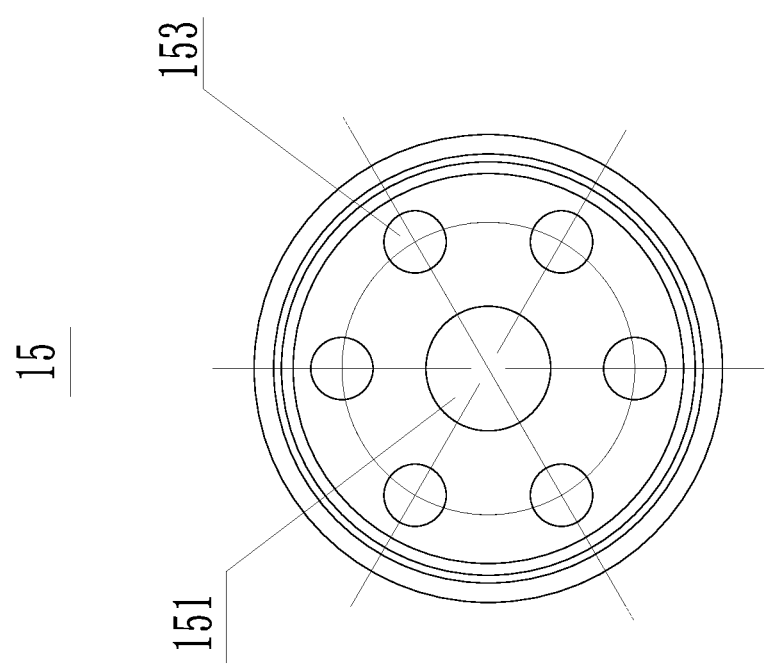
FIG. 13 is a front view of the sealing connection interface as shown in FIG. 11.

As shown in FIG. 11, the ablation needle 1 includes a needle body 18 and a handle 12 which are in connection via a sealing connection interface 15, and the sealing connection interface 15 is provided in the handle 12. Referring to FIG. 12 and FIG. 13, the sealing connection interface 15 includes a first opening 151 and a second opening 152 which are provided in one metal tube, and the line in the needle body 18 passes through the first opening 151 and the second opening 152 sequentially. The sealing connection interface 15 also includes a vacuum sealed opening 153 provided in the circumferential direction of the first opening 151. The vacuum sealed opening 153 includes a large hole 153a and a small hole 153b, which are configured to be stepped holes. The axes of the large hole 153a and the small hole 153b are in parallel to the axis of the first opening 151, and the small hole 153b is in communication with the second opening 152.

As shown in FIG. 12, the sealing connection interface 15 is approximately of a columnar structure, the axial directions of the first opening 151 and the second opening 152 coincides with each other, and the axial direction of the first opening 151 is in parallel to the axial direction of the vacuum sealed opening 153, that is, the extension direction of the first opening 151 is the same as that of the vacuum sealed opening 153, and therefore, the sealing connection interface 15 forms an approximately columnar structure, and there is no protrusion in the radial direction thereof, that is, there is no need to arrange any structure in the radial direction, for example, a extraction port structure. Since the sealing connection interface 15 can realize annular sealing connection without the need to arrange a protrusion in the radial direction, the needle body 18 and the handle 12 can be docked in such a way that the axes coincide with each other, such that the overall structure of the ablation needle 1 is more concise, and the technical problem in the industry of only a protrusion joint being available all the time is also solved. The ablation needle 1 can be configured as a straight columnar structure benefiting from the sealing connection interface 15. Compared with an existing ablation needle having a right-angle bend, the ablation needle 1 of the disclosure can be applied to heart tissue ablation treatment more conveniently.

In addition, the large hole 153a is provided with a solder. When vacuum sealing is performed, the solder is melted by heating, so that the melted solder flows into the small hole 153b and seals the small hole 153b, thereby achieving the aim of sealing. The solder can be a glass solder. In addition, an alternative sealing method such as oxygen-free copper and a glass tube can also be used.

Figure 14:
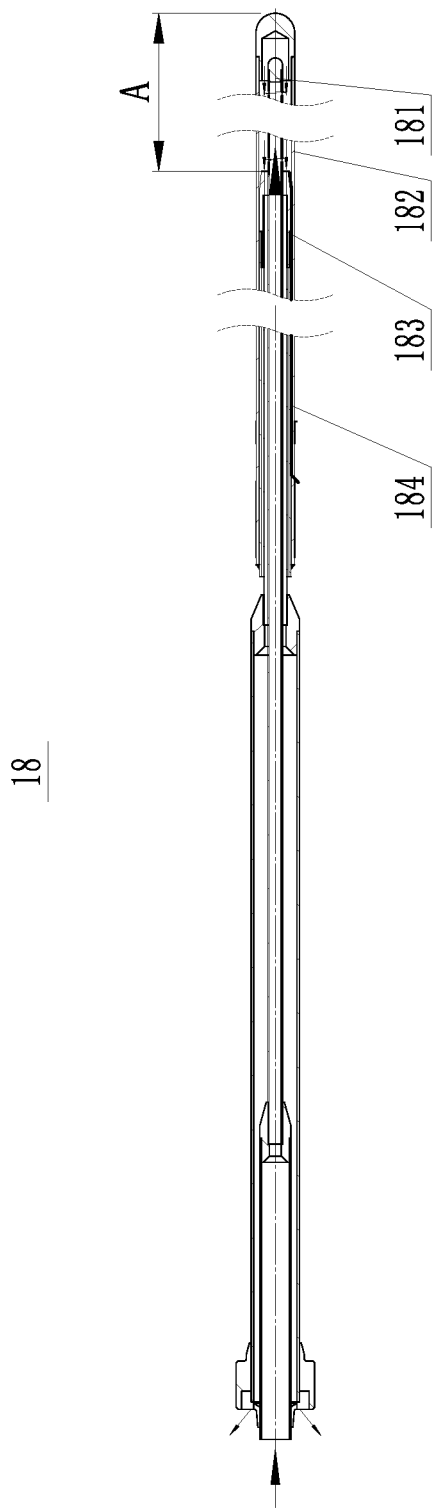
FIG. 14 and FIG. 15 are cutaway views of a needle body as shown in FIG. 11.
Figure 15:
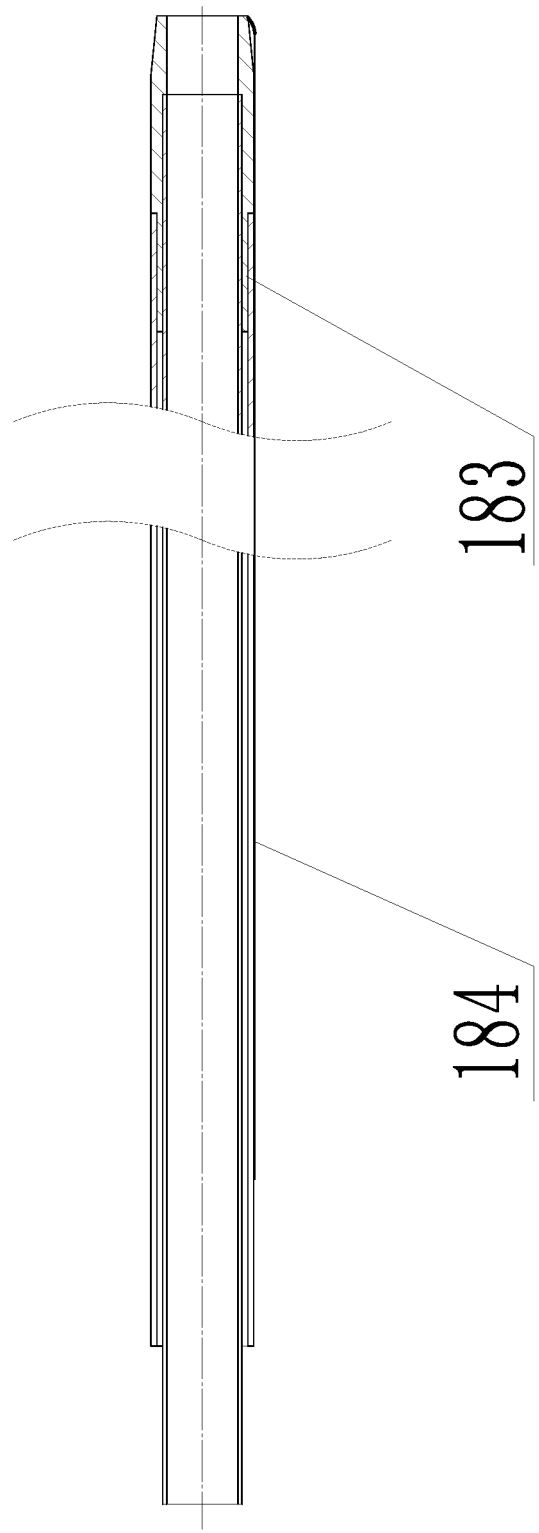
Figure 16:
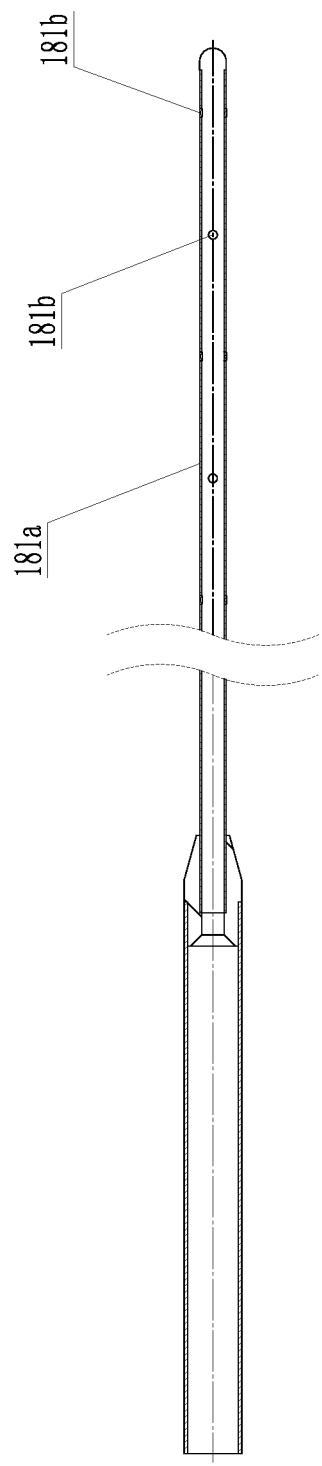
FIG. 16 is a schematic structural diagram of an inflow tube as shown in FIG. 11.

As shown in FIG. 14, FIG. 15, and FIG. 16, the needle body 18 includes an inflow tube 181, a cannula 182 and a vacuum cannula 183.

The inflow tube 181 is in communication with the first delivery tube 26, and the inflow tube 181 includes a treatment tube section 181a (the treatment tube section 181a corresponding to the region A as shown in FIG. 14, i.e. the treatment region) and a non-treatment tube section (the non-treatment tube section corresponding to the region B as shown in FIG. 11, i.e. the non-treatment region).

The cannula 182 is sheathed at the treatment tube section 181a of the inflow tube 181, and the vacuum cannula 183 is sheathed at the non-treatment tube section of the inflow tube 181. Through the thermal insulation function of the vacuum cannula 183, the temperature of the non-treatment tube section remains a right temperature a hand-holding operation can be performed.

The cannula 182 can be sheathed outside the vacuum cannula 183 and be fixed to the vacuum cannula 183 in the sealing manner. Preferably, the cannula 182 is fixed to the vacuum cannula 183 in the sealing manner through welding.

In some embodiments, the cannula 182 is configured to be a plastic hose, which can be shaped for lesions of different shapes, so as to construct an expected shape fitting a target position. The cannula 182 is more applicable to an ablation treatment such as heart tissue ablation or skin tissue ablation.

Figure 20:
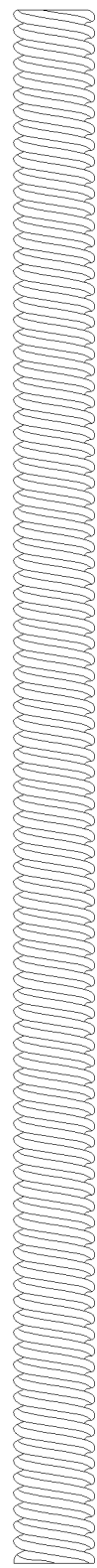
FIG. 20 is a schematic structural diagram of a cannula in an embodiment of the disclosure.

In some preferred embodiments, as shown in FIG. 20, the cannula 182 is configured to be a flexible metal hose. The number of times of bending and the angle of bending when the hose is shaped are not limited, and no damage is caused by the number of times of bending being too large or the angle of bending being too large. Therefore, the flexible metal hose can be deformed many times and by a large angle, so as to more effectively fit a lesion area and a cell tissue with abnormal electrophysiology.

In some embodiments, the cannula 182 can be configured as a rigid tube, which can be positioned by imaging and punctured into the lesion tissue for minimally invasive ablation treatment.

As shown in FIG. 14, a temperature measurement thermocouple 184 is arranged between the vacuum cannula 183 and the cannula 182, the temperature measurement thermocouple 184 is disposed along an outer wall of the vacuum cannula 183 and an inner wall of the cannula 182, and is connected to a temperature transmitter 13 on the handle, with the temperature transmitter 13 being located in the non-treatment region of the cryoablation needle 1. The temperature transmitter 13 can be fixedly connected to the sealing connection interface 15 via the protective sleeve 17.

Preferably, the temperature measurement thermocouple 184 can be a T-shaped thermocouple.

In addition, the sealing connection interface 15 can also be provided with a temperature display device 14, which is electrically connected to the temperature transmitter 13. Therefore, the temperature during a treatment process can be displayed on the temperature display device 14 in real time, so as to facilitate the user in observation at any time during a surgery.

Therefore, the ablation needle 1 of the disclosure can implement a temperature measurement function and the function of monitoring temperature in real time.

Furthermore, as shown in FIG. 11, an end of the handle 12 that is away from the needle body 18 is provided with a quick male coupling 11, which is connected to the quick coupling 21 described above in the fitting manner, such that the ablation needle 1 can be quickly connected to the working medium transmission device 2. A groove is provided in an outer wall of the quick male coupling 11, and a sealing ring 16 is arranged in the groove. When the quick male coupling 11 is connected to the quick coupling 21 in the fitting manner, the sealing ring 16 fits the tapered inner wall of the fitting hole 211 described above, so as to have the sealing function.

The sealing ring 16 can be an O-shaped ring, which can be made of fluororubber, polytetrafluoroethylene or other sealing materials.

As shown in FIG. 16, the treatment tube section 181a is provided with a plurality of formation holes 181b. A working medium in the treatment tube section 181a flows to a space between the treatment tube section 181a and the cannula 182 through the formation holes 181b, so that icicles for treatment can be formed at a position, in contact with the target area, of an outer wall of the cannula 182 (for example, a tissue fluid or a cell fluid in the target area freezing to form an icicle structure).

The working medium in the first delivery tube 26 is delivered to the treatment tube section 181a and flows to the space between the treatment tube section 181a and the cannula 182 through the formation holes 181b. The working medium between the treatment tube section 181a and the cannula 182, after the heat exchange treatment of tissue cells in the target area is performed, flows back to the second delivery tube 24 in a direction opposite to the flowing direction of the working medium flowing into the treatment tube section 181a.

In some embodiments, the plurality of formation holes 181b are provided at equal intervals in the axial direction of the treatment tube section 181a, and one or more formation holes are provided on one and the same radial cross-section of the treatment tube section 181a.

In some embodiments, the plurality of formation holes 181b are provided in a clockwise or counterclockwise spiral manner in the circumferential direction of the treatment tube section 181a.

By using the provision of the formation holes 181b, the disclosure breaks the limitation in an existing technique of a working medium only flowing out of an end portion of a treatment tube section. In the disclosure, the working medium can flow out from different positions of the treatment tube section 181a, such that icicles for treatment can be quickly formed at a position, in contact with the target area, of the outer wall of the cannula 182. These formation holes 181b are provided in a special manner, such that uniform columnar ice bodies, rather than conventional ice balls (spherical ice bodies), can be formed at the position, in contact with the target area, of the outer wall of the cannula 182, so as to better facilitate an ablation treatment for a linear lesion tissue and columnar lesion tissue during an ablation treatment for the lesion tissue. The lesion tissue can be a solid tumor, superficial soft tissue, and the like.

Several particular embodiments of the provision of the formation holes 181b will be described below. It should be understood that the embodiments below are merely used as examples to illustrate the provision manner of the disclosure, and are not intended to limit the disclosure.

Embodiment 1

In the embodiment, the plurality of formation holes 181b provided on the treatment tube section 181a are provided in the following manner.

A plurality of (even numbers of) formation holes 181b are provided on one and the same radial cross-section, and the axes of opposite formation holes 181b on one and the same radial cross-section coincide each other. A plurality of formation holes 181b are provided at equal intervals in the axial direction.

Figure 17:
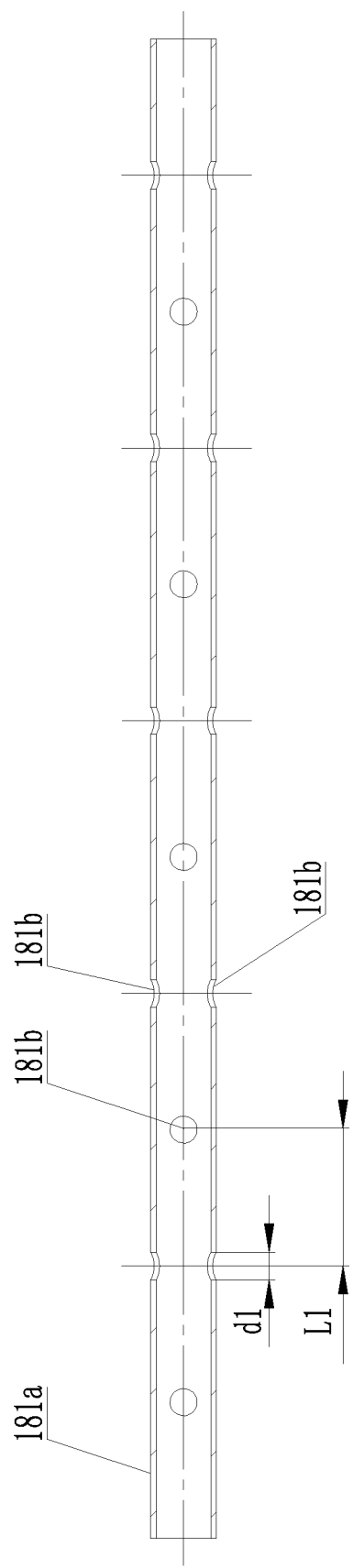
FIG. 17 is a schematic diagram of a distribution manner of formation holes in a first embodiment of the disclosure.

As shown in FIG. 17, four formation holes 181b are provided on one and the same radial cross-section, and the axes of opposite formation holes 181b on one and the same radial cross-section coincide with each other. A plurality of formation holes 181b are provided at equal intervals in the axial direction. The aperture d1 of the formation hole 181b is 0.3 mm to 0.4 mm, and preferably 0.4 mm. The axial spacing L1 between two adjacent formation holes 181b in the axial direction is 6 mm to 12 mm, and preferably 10 mm Embodiment 2

In the embodiment, the plurality of formation holes 181b provided on the treatment tube section 181a are provided in the following manner.

One or more formation holes 181b are provided on one and the same radial cross-section, and the axes of opposite formation holes 181b on one and the same radial cross-section do not coincide with each other. A plurality of formation holes 181b are provided at equal intervals in the axial direction.

Figure 18:
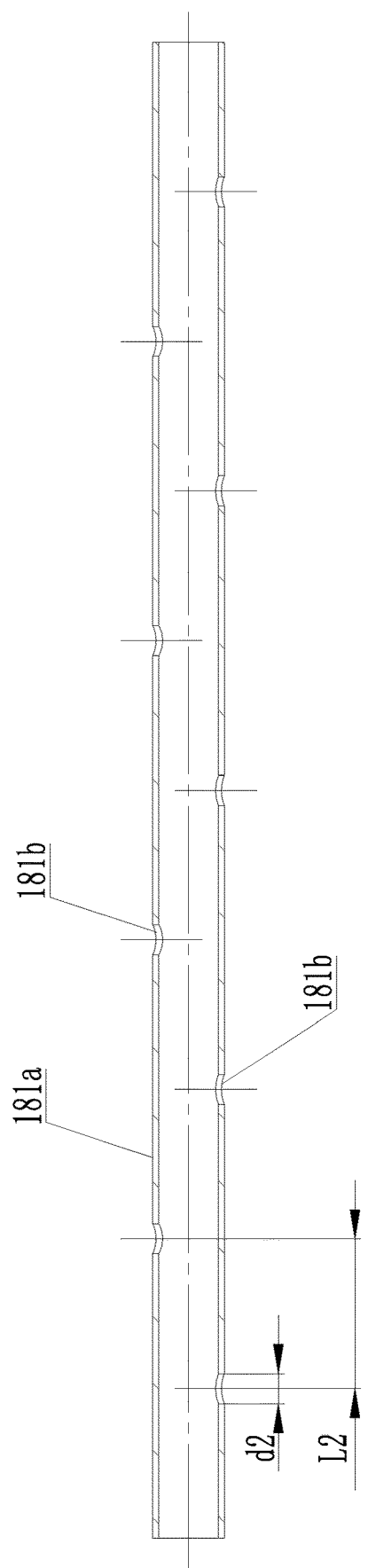
FIG. 18 is a schematic diagram of a distribution manner of formation holes in a second embodiment of the disclosure.

As shown in FIG. 18, one formation hole 181b is provided on one and the same radial cross-section, and a plurality of formation holes 181b are provided at equal intervals in the axial direction. The aperture d2 of the formation hole 181b is 0.3 mm to 0.4 mm, and preferably 0.4 mm. The axial spacing L2 between two adjacent formation holes 181b in the axial direction is 5 mm to 10 mm, and preferably 5 mm Embodiment 3

In the embodiment, the plurality of formation holes 181b provided on the treatment tube section 181a are provided in the following manner.

Figure 19:
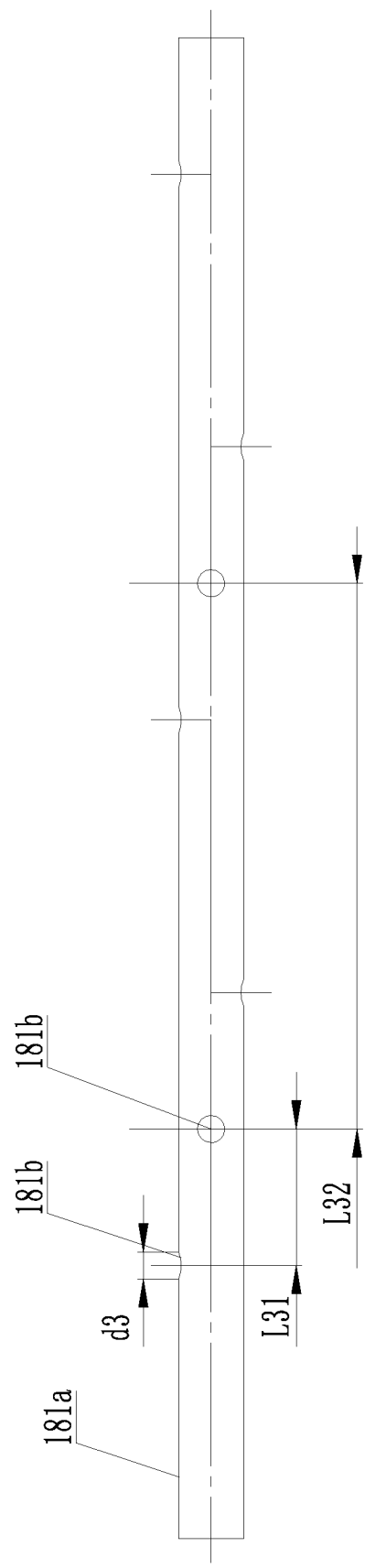
FIG. 19 is a schematic diagram of a distribution manner of formation holes in a third embodiment of the disclosure.

A plurality of formation holes 181b are provided in a counterclockwise/clockwise spiral manner in the circumferential direction of the treatment tube section 181a. As shown in FIG. 19, three formation holes 181b are in one group, and the three formation holes 181b are staggered with each other by 90 degrees in the axial direction. Multiple groups of formation holes 181b are provided at equal intervals in the axial direction.

The aperture d3 of the formation hole 181b is 0.3 mm to 0.4 mm, and preferably 0.4 mm. The axial spacing L31 between formation holes 181b in each group is 5 mm to 8 mm, and preferably 5 mm. The axial spacing L32 between formation holes 181b, corresponding to each other, in different groups is 20 mm to 32 mm, and preferably 20 mm Comparative Example 1

The plurality of formation holes 181b provided on the treatment tube section 181a are provided in the following manner.

A plurality of (even numbers of) formation holes 181b are provided on one and the same radial cross-section, and the axes of opposite formation holes 181b on one and the same radial cross-section coincide each other. A plurality of formation holes 181b are provided at equal intervals in the axial direction.

Four formation holes 181b are provided on one and the same radial cross-section, and the axes of opposite formation holes 181b on one and the same radial cross-section coincide each other. A plurality of formation holes 181b are provided at equal intervals in the axial direction. The aperture d1 of the formation hole 181b is 0.6 mm, and the axial spacing L1 between two adjacent formation holes 181b in the axial direction is 15 mm

TABLE 1

Embodiment 1 and Comparative example 1

| Parameter | Embodiment | |
|---|---|---|
| | Embodiment 1 | Comparative example 1 |
| Aperture d1 (mm) | 0.4 | 0.6 |
| Axial hole spacing L1 (mm) | 10 | 15 |
| Working medium frozen shape | Uniform columnar body | Taper |
| Time (s) ice balls cover a treatment region | about 20 s | about 40 s |

It can be seen from table 1 that, in comparative example 1 and embodiment 1, the provision manners of the formation holes 181b are the same, whereas the apertures and the axial hole spacings are different; and comparative example 1 cannot quickly obtain uniform columnar icicle, whereas embodiment 1 of the disclosure can obviously better satisfy the requirements form time and a treatment effect during a heart ablation surgery.

Comparative Example 2

One or more formation holes 181b are provided on one and the same radial cross-section, and the axes of opposite formation holes 181b on one and the same radial cross-section do not coincide with each other. A plurality of formation holes 181b are provided at equal intervals in the axial direction.

One formation hole 181b is provided on one and the same radial cross-section, and a plurality of formation holes 181b are provided at equal intervals in the axial direction. The aperture d2 of the formation hole 181b is 0.6 mm. The axial spacing L2 between two adjacent formation holes 181b in the axial direction is 15 mm

TABLE 2

Embodiment 2 and Comparative example 2

| | Embodiment | |
|---|---|---|
| Parameter | Embodiment 2 | Comparative example 2 |
| Aperture d2 (mm) | 0.4 | 0.6 |
| Axial hole spacing L2 (mm) | 5 | 15 |
| Working medium frozen shape | Uniform columnar body | Gourd |
| Time (s) ice balls cover a treatment region | about 20 s | In a gourd shape within 1 min |

It can be seen from table 2 that, in comparative example 2 and embodiment 2, the provision manners of the formation holes 181*b* are the same, whereas the apertures and the axial hole spacings are different; and comparative example 2 cannot quickly obtain uniform columnar icicle, whereas embodiment 2 of the disclosure can obviously better satisfy the requirements form time and a treatment effect during a heart ablation surgery.

Comparative Example 3

The plurality of formation holes 181*b* provided on the treatment tube section 181*a* are provided in the following manner.

The plurality of formation holes 181*b* are provided in a counterclockwise spiral manner in the circumferential direction of the treatment tube section 181*a*. Three formation holes 181*b* are in one group, and the three formation holes 181*b* are staggered with each other by 90 degrees in the axial direction. Multiple groups of formation holes 181*b* are provided at equal intervals in the axial direction.

The aperture d3 of the formation hole 181*b* is 0.6 mm, and the axial spacing L31 between formation holes 181*b* in each group is 15 mm. The axial spacing L32 between formation holes 181*b*, corresponding to each other, in different groups is 25 mm

TABLE 3

Embodiment 3 and Comparative example 3

| | Embodiment | |
|---|---|---|
| Parameter | Embodiment 3 | Comparative example 3 |
| Aperture d3 (mm) | 0.4 | 0.6 |
| Axial hole spacing L31 (mm) | 5 | 15 |
| Axial hole spacing L32 (mm) | 20 | 25 |
| Working medium frozen shape | Uniform columnar body | Taper/Gourd |
| Time (s) ice balls cover a treatment region | about 20 s | In a gourd shape within 1 min |

It can be seen from table 3 that, in comparative example 3 and embodiment 3, the provision manners of the formation holes 181*b* are the same, whereas the apertures and the axial hole spacings are different; and comparative example 3 cannot quickly obtain uniform columnar icicle, whereas embodiment 1 of the disclosure can obviously better satisfy the requirements form time and a treatment effect during a heart ablation surgery.

Although the disclosure has been described with reference to the preferred embodiments, various modifications can be made in the disclosure and the components in the disclosure can be replaced with equivalents without departing from the scope of the disclosure. In particular, all the technical features mentioned in the various embodiments can be combined in any manner as long as there is no structural conflict. The present disclosure is not limited to the specific examples disclosed herein, but covers all the technical solutions falling within the scope of the appended claims.

The invention claimed is:

1. An ablation device, comprising an ablation needle (1) and a working medium transmission device (2) connected to the ablation needle (1), wherein the working medium transmission device (2) comprises:

a first delivery tube (26), which is used for delivering a working medium to the ablation needle (1);

a second delivery tube (24), which is used for receiving and discharging a working medium that is output from the ablation needle (1) after treatment is performed; and a connection tube (27), a first end of which is connected to the ablation needle (1), and a second end of which is respectively connected to the first delivery tube (26) and the second delivery tube (24), wherein the first delivery tube (26) and the second delivery tube (24) are configured to be of split structures that are independent of each other, the ablation needle (1) comprising a needle body (18) and a handle (12), which are in connection via a sealing connection interface (15), the needle body (18) comprising:

an inflow tube (181), which is in communication with the first delivery tube (26), wherein the inflow tube (181) comprises a treatment tube section (181*a*) and a non-treatment tube section;

a cannula (182), which is sheathed at the treatment tube section (181*a*) of the inflow tube (181); and a vacuum cannula (183), which is sheathed at the non-treatment tube section of the inflow tube (181), wherein the treatment tube section (181*a*) is provided with a plurality of formation holes (181*b*), and a working medium in the treatment tube section (181*a*) flows to a space between the treatment tube section (181*a*) and the cannula (182) through the formation holes (181*b*), so that icicles for treatment can be formed on an outer wall of the cannula (182), wherein the second delivery tube (24) comprises:

an outer cannula (241), which is arranged at a side of the connection tube (27) that is away from the ablation needle (1), wherein a heat exchange device (25) is arranged in the outer cannula (241); and a second conduit (242), wherein at least part of the second conduit (242) extends from the second end of the connection tube (27) into the connection tube (27), and at least part of the second conduit (242) extends into the outer cannula (241) and is connected to the heat exchange device (25), so that the working medium in the ablation needle (1) after the treatment is performed can be delivered to the heat exchange device (25) through the second conduit (242), and the working medium after being subjected to heat exchange in the heat exchange device (25) can directly be discharged into the environment.

2. The Ablation device according to claim 1, wherein the heat exchange device (25) is internally provided with a path (251) for the flowing of the working medium after the treatment is performed, one end of the path (251) is in communication with the second conduit (242), the other end of the path (251) is in communication with the environment, and the path (251) comprises one or more of a spiral path, a snakelike path, a clip-shaped path, and a waved path.

3. The Ablation device according to claim 2, wherein the second end of the connection tube (27) is also provided with a diffluence device (23), the diffluence device (23) comprising:
- a seal (231), which is arranged at the second end of the connection tube (27) in a sealing manner;
- a first through hole (232), which is arranged on the seal (231) and axially passes through the seal (231) for being connected to the first delivery tube (26) in a fitting manner;
- a protrusion portion (233), which axially extends from an end portion of the seal (231) for being engaged with an inner wall of the outer cannula (241); and
- a second through hole (234), which is arranged on the seal (231) and axially passes through the seal (231) and the protrusion portion (233) for being connected to the second conduit (242) in a fitting manner.

4. The Ablation device according to claim 1, wherein the connection tube (27) is internally provided with a conflux device (22) that is in communication with the ablation needle (1), the first delivery tube (26) and the second delivery tube (24) respectively extend from the second end of the connection tube (27) into the connection tube (27) and are in communication with the conflux device (22), so as to deliver a working medium into the ablation needle (1) or receiving the working medium from the ablation needle (1).

5. The Ablation device according to claim 4, wherein the conflux device (22) comprises a conflux tube (221) arranged in the connection tube (27), a first end of the conflux tube (221) extends out of the connection tube (27) and is connected to a quick coupling (21), and the quick coupling (21) is connected to the ablation needle (1) in a fitting manner;
- a second end of the conflux tube (221) is provided with a first connection hole (221*a*) for being connected to the first delivery tube (26) in a fitting manner, and a second connection hole (221*b*) for being connected to the second conduit (242) in a fitting manner; the first connection hole (221*a*) and the second connection hole (221*b*) are arranged side by side in the radial direction of the conflux tube (221); and
- the conflux tube (221) is also internally provided with a drainage hole (221*c*), with the drainage hole (221*c*) being connected to the first connection hole (221*a*) in a lapped manner.

6. The Ablation device according to claim 5, wherein the quick coupling (21) comprises a fitting hole (211) that is connected to the ablation needle (1) in a fitting manner, and at least part of an inner wall of the fitting hole (211) in the axial direction tapers, so as to form tapered sealing with a sealing ring (16) on the ablation needle (1).

7. The Ablation device according to claim 1, wherein the sealing connection interface (15) is provided in the handle (12), the sealing connection interface (15) comprises a first opening (151) and a second opening (152), which are arranged in one metal tube, and a line in the needle body (18) sequentially passes through the first opening (151) and the second opening (152); and
- the sealing connection interface (15) also comprises a vacuum sealed opening (153) provided in the circumferential direction of the first opening (151), the vacuum sealed opening (153) comprises a large hole (153*a*) and a small hole (153*b*), which are configured to be stepped holes, the axes of the large hole (153*a*) and the small hole (153*b*) are in parallel to the axis of the first opening (151), and the small hole (153*b*) is in communication with the second opening (152).

8. The Ablation device according to claim 7, wherein the cannula (182) is configured to be a plastic hose or a flexible metal hose.

9. The ablation device according to claim 1, wherein the plurality of formation holes (181*b*) are distributed in one or more of the following manners:
- the plurality of formation holes (181*b*) are provided at equal intervals in the axial direction of the treatment tube section (181*a*), and one or more formation holes are provided on one and the same radial cross-section of the treatment tube section (181*a*); and
- the plurality of formation holes are provided in a clockwise or counterclockwise spiral manner in the circumferential direction of the treatment tube section (181*a*).

\* \* \* \* \*